United States Patent [19]

Ling

[11] 4,298,593

[45] Nov. 3, 1981

[54] REAGENTS AND METHODS UTILIZING LABELED FAB BOUND TO ANTIGENS

[75] Inventor: Chung-Mei Ling, Chicago, Ill.

[73] Assignee: Abbott Laboratories, North Chicago, Ill.

[21] Appl. No.: 68,772

[22] Filed: Aug. 21, 1979

[51] Int. Cl.$^3$ ............... A61K 43/00; G01N 33/48; G01T 1/00
[52] U.S. Cl. ................. 424/1; 23/230 B; 260/112 B; 424/12; 435/7
[58] Field of Search .............. 424/1, 1.5, 12; 23/230 B; 260/112 B; 435/7

[56] References Cited

U.S. PATENT DOCUMENTS 4,166,106  8/1979  Sedlacek et al. .......... 23/230 B
4,193,982  3/1980  Avrameas et al. ......... 23/230 B

OTHER PUBLICATIONS

Gonatas et al., J. Histochem. Cytochem., 22 #11 1974, pp. 999–1009.
Zaitlin, Immunochem., 8(6) 1971, pp. 569–573.

*Primary Examiner*—Deborah L. Kyle
*Assistant Examiner*—Christine M. Nucker
*Attorney, Agent, or Firm*—John J. McDonnell

[57] ABSTRACT

This invention involves an improvement in a method for immunochemically assaying a member of an antigen-antibody binding pair in serum or plasma which utilizes labeled antigen having a plurality of antigenic binding sites as the indicating reagent, the improvement comprising employing the antigen immunochemically bound to labeled Fab as the indicating reagent. This invention also encompasses reagents useful in practicing the above method. These methods and reagents are particularly useful in hepatitis detection.

4 Claims, No Drawings

REAGENTS AND METHODS UTILIZING LABELED FAB BOUND TO ANTIGENS

BACKGROUND OF THE INVENTION

Papain digestions of immunoglobulin splits the immunoglobulin into protein fragments identified as Fab (fraction antigen binding) and Fc (fraction crystallizing). The Fab fragment binds to antigen but does not yield agglutinating or precipitating aggregates. The Fab fraction has been separated and labeled with $H^3$, $I^{125}$, and peroxidase enzyme Immunochem 8(6) 509-73 (1971) and Journal of Histochemistry and Cytochemistry 22 (11) 1974, p. 999. These labeled Fab fragments have been used to label antigens on cells for ultrastructure autoradiography studies.

SUMMARY OF THE INVENTION

This invention involves an improvement in a method for immunochemically assaying a member of an antigen-antibody binding pair in serum or plasma which utilizes labeled antigen having plurality of antigenic binding sites as the indicating reagent, the improvement comprising employing the antigen immunochemically bound to labeled Fab as the indicating reagent. This invention also encompasses reagents useful in practicing the above method. These methods and reagents are particularly useful in hepatitis detection.

DETAILED DESCRIPTION OF THE INVENTION

The reagents of the present invention are represented by the formula

Antigen-Fab-x

The Fab fragment is prepared by raising antiserum to the antigen, isolating the IgG fragment and digesting that fraction in papain to split the IgG in 2 Fab and in Fc fragment. The Fab fraction is separated and labeled with an appropriate indicator. For example, the Journal of Histochemistry and Cytochemistry describes the labeling on Fab with $I^{125}$ and also with peroxidase enzymes.

The antigen must have a plurality of antigenic binding sites and labeled Fab is immunochemically bound to a portion of the antigenic binding sites. The antigen moiety of the complex, antigen-Fab-X, must have antigenic binding sites available for further immunochemical reaction. In other words, if all of the antigenic binding sites were occupied with Fab-x the complex would not be useful as contemplated by the present invention.

Typical antigens useful in manufacturing reagants are: hepatitis B surface antigen (HBsAg), hepatitis B core antigen (HBcAg), hepatitis A viral antigen (HAV-Ag). It should also be understood that antibodies to these antigens can serve as antigenic substances in the complex in which case antibodies to antigen such as anti-HBs, anti-HBc, and anti-HAV are raised and the IgG fraction of the antibodies so raised are digested with papain to provide Fab specifically binding to $HB_sAg$, etc.

The Fab may be radioactively labeled with isotopes such as $I^{125}$ or $I^{131}$ by convention techniques for labeling proteins with these isotopes. Fab may be labeled with enzymes such as horseradish peroxidase or alkaline-phosphatase by conventional methods for conjugating enzymes to protein. Fab may also be labeled with fluorescent dyes such as fluorescein and xanthene dyes by conventional techniques, for example, forming amide or ester bonds between a functional group on the Fab protein and a function group on the dye.

It is highly desirable to titrate the antigen and labeled Fab to obtain reagents of optimum sensitivity. This involves balancing the amount of labeled Fab bound to the antigen with the number of remaining antigenic sites to obtain the best performance.

In a typical preparation, hepatitis B core antibody (anti-HBc) is from human serum and the IgG fraction is separated and digested with papain. The Fab fraction is separated and labeled with $I^{125}$ to provide Fab-$I^{125}$. Fab-$I^{125}$ is reacted with HBcAg to provide HBcAg-Fab-$I^{125}$ wherein antigenic binding sites on the HBcAg moiety are available for immunochemical binding.

A polystyrene bead is incubated with test serum, and the bead is washed and reacted with the above reagent. After incubation, the bead is washed and counted. Significant increases in radioactivity as compared to beads not exposed to serum is a positive test for the presence of hepatitis.

In order to prepare HBcAg-Fab-$I^{125}$ with desired qualities, various ratios of HBcAg and Fab-$I^{125}$ solutions are used to prepare HBcAg-Fab-$I^{125}$. The resulting preparations are tested with beads pre-loaded with a fixed amount of anti-HBc as shown in Table I and II below. From the results shown in Table I, if maximum count per minute (cpm) ratio of positive to negative sample is desired, the most desirable combination is preparation (4).

TABLE I

Use of HBcAG-Fab-$I^{125}$ complexes made from varying amounts of $I^{125}$ labeled Fab of anti-HBc and constant amount of HBcAg.

| No. | Volumes of HBcAg (ml) | Amounts of Fab-$I^{125}$ (cpm) | HBcAg-Fab $I^{125}$ Anti-HBc Beads | Uptake by Plain Beads | Net cpm | +/− ratio |
|---|---|---|---|---|---|---|
| (1) | 0.5 | 2.72 × 10⁶ | 15,249 | 4,723 | 10,526 | 3.2 |
| (2) | 0.5 | 1.36 × 10⁶ | 8,324 | 2,629 | 5,695 | 3.2 |
| (3) | 0.5 | 0.68 × 10⁶ | 7,377 | 1,583 | 5,794 | 4.7 |
| (4) | 0.5 | 0.34 × 10⁶ | 4,621 | 807 | 3,814 | 5.7 |
| (5) | 0.5 | 0.17 × 10⁶ | 2,786 | 524 | 2,262 | 5.3 |

TABLE II

Use of HBcAg-Fab-$I^{125}$ complexes made from constant amounts of $I^{125}$ labeled Fab of anti-HBc and varying amounts of HBcAg.

| Volumes of HBcAg (ml) | Amounts of Fab-$I^{125}$ (cpm) | HBcAg-Fab-$I^{125}$ Uptake by Anti-HBc beads | |
|---|---|---|---|
| | | Gross cpm | Net cpm |
| 0.70 | 1.25 × 10⁶ | 13,028 | 8,484 |
| 0.35 | 1.25 × 10⁶ | 7,254 | 2,900 |
| 0.18 | 1.25 × 10⁶ | 5,581 | 1,227 |
| 0.09 | 1.25 × 10⁶ | 4,354 | 0 |

TABLE II-continued

Use of HBcAg-Fab-$I^{125}$ complexes made from constant amounts of $I^{125}$ labeled Fab of anti-HBc and varying amounts of HBcAg.

| Volumes of HBcAg (ml) | Amounts of Fab-$I^{125}$ (cpm) | HBcAg-Fab-$I^{125}$ Uptake by Anti-HBc beads | |
|---|---|---|---|
| | | Gross cpm | Net cpm |
| 0 | 1.25 × 10$^6$ | 4,544 | 0 |

The following examples are set forth to illustrate the invention and are not intended to limit the invention in spirit or scope. Those skilled in the immunoassay arts will recognize the applicability of methods and reagents of this invention to a wide variety of solid phase and precipitation immunoassay techniques which utilize labeled antigen having a plurality of antigenic binding sites as an indicator reagent.

EXAMPLE 1

Preparation of HBcAg-Fab-$I^{125}$

To 3 ml of the anti-HBc preparation is added the following: 0.02 ml of papain (7.29 mg/ml), 0.5 ml of 0.5 M phosphate buffer at pH7.5, 0.5 ml of water, 0.02 ml of 0.4 M EDTA at pH 7.6, and 0.02 ml of 0.2 M cysteine-HCl. The resulting mixture is in a total volume of approximately 4 ml and is then incubated overnight at 37° C. The Fab fragments of the anti-HBc are isolated from the mixture by column chromatography. These Fab fragments are then iodinated with Iodine-125 following the method of Marchalonis [Biochem. J. 173, 299 (1969)], producing thereby Fab-$I^{125}$ of anti-HBc.

A 0.2 ml of HB$_c$Ag and 5 ml of Fab-$^{125}$I of anti-HB$_c$ is mixed with 4.8 ml of solution containing 1% Tween-20, 1% bovine serum albumin in 0.01 M Tris-0.15 M saline-0.001 M EDTA buffer at pH 7.5. The resulting mixture is allowed to incubate at room temperature overnight. The mixture is then layered on a 15%–65% linear sucrose gradient and centrifuged in a Beckman SW-27 rotor at 25,000 rpm for 5 hours. The contents of each centrifuge tube are fractionated and the fractions containing HB$_c$Ag-Fab$^{125}$I are obtained and used to measure the presence or absence of anti-HB$_c$ in samples as exemplified in Table III.

TABLE III

Use of sucrose gradient purified HB$_c$Ag-Fab-$^{125}$I-complex in the determination of anti-HB$_c$.

| Sample No. | HB$_c$Ag-Fab-$^{125}$I-complex uptake by the | |
|---|---|---|
| | Anti-HB$_c$ beads (cpm) | Negative serum beads (cpm) |
| 1 | 1,692 | 799 |
| 2 | 1,564 | 872 |

EXAMPLE 2

Preparation of HAV-Fab-$I^{125}$

To 3 ml of the anti-HAV preparation is added the following: 0.5 ml of 0.5 M phosphate buffer at pH 7.5, 0.5 ml of water, 0.02 ml of 0.4 M EDTA at pH 7.0, 0.02 ml of 0.2 M cysteine-HCl, and 0.02 ml of papain (7.29 mg/ml). The resulting reaction mixture in a total volume of approximately 4.0 ml is incubated overnight at 37° C. The reaction of the mixture is then stopped by chilling and freezing. Thereafter, 0.4 g dry weight of Staphylococcus aureus containing protein A is added to the mixure which has been brought to room temperature. The bacteria is mixed in the mixture and absorbs Fc fragments and undigested IgG. The mixture is then centrifuged at 1000×g for about 10 minutes, precipitating the bacteria and bacteria complexes. The supernatant containing Fab fragments is removed and iodinated with Iodine-125 following the method of Marcholomis [Biochem. J. 113, 299 (1969)], producing thereby Fab-$I^{125}$ of anti-HAV. The latter is mixed into 4.8 ml of solution containing 1% Tween-20, 1% bovine serum albumin in 0.01 M Tris-0.15 M saline-0.001 M EDTA buffer at pH 7.5. The resulting mixture is allowed to incubate at room temperature overnight. The mixture is then layered on a 15%–65% linear sucrose gradient and centrifuged in a Beckman SW-27 rotor at 25,000 rpm for 5 hours. The contents of each centrifuge tube are fractionated and the fractions containing HAV-Ag-Fab-$I^{125}$ are obtained.

EXAMPLE 3

Assay for Hepatitis B Core Antibody (Anti-HB$_c$)

A polystyrene bead approximately 6 mm in diameter is placed in about 0.2 ml of a serum or plasma (diluted or undiluted) sample, positive for anti-HB$_c$. The sample is allowed to coat the bead for approximately 24 hours at room temperature. The sample is separated from the bead by aspiration of the sample solution. The bead is then washed with several volumes of water. Thereafter the bead is incubated with a 0.2 ml solution of HB$_c$-Ag-Fab-$I^{125}$ for one to 24 hours at room temperature. The bead and solution are separated by simple aspiration of the solution, and the bead is washed with several volumes of water. Thereafter, the radioactivity associated with the bead is determined in a gamma radiation counter. Presence of anti-HB$_c$ in the serum or plasma sample is signified by increased radioactivity over an anti-HB$_c$ negative sample.

EXAMPLE 4

Assay for IgM Anti-HAV

A polystyrene bead approximately 6 mm in diameter is coated with rabbit anti-IgM specific for μ-chain. 0.2 ml sample of human serum, diluted 1:4000, is incubated overnight with the bead. The bead is washed with several volumes of water. Thereafter the bead is incubated with 0.2 ml of HAV-Fab-$I^{125}$ complex (Example 1) for 4 hours at room temperature. The bead and solution are separated, the bead washed with water and counted in a γ-spectroscope. The presence of Anti-HAV in the sample is signified by increased radioactivity over anti-HAV IgM negative samples.

EXAMPLE 5

Assay for IgM Anti-HB$_c$

Same as Example 4, except using HB$_c$Ag-Fab-$I^{125}$ complex instead.

What is claimed is:

1. An immunoassay reagent comprising a solution of an antigen having a plurality of antigenic binding sites wherein a portion of the binding sites are immunochemically bound to labeled Fab and other immunochemically binding sites are available for binding to antibodies.

2. An immunoassay reagent, according to claim 1, which is hepatitis core antigen immunochemically bound to labeled Fab.

3. An immunoassay reagent, according to claim 1, which is hepatitis A viral antigen immunochemically bound to labeled Fab.

4. A method for preparing an immunoassay reagent comprising immunochemically reacting labeled Fab with an antigen in solution wherein the antigen has a plurality of antigenic binding sites and wherein a portion of said antigenic binding sites remain available for immunochemically binding to antibody after reaction with the labeled Fab.

* * * * *